(12) United States Patent
Zigon et al.

(10) Patent No.: US 8,214,323 B2
(45) Date of Patent: Jul. 3, 2012

(54) EXTENSIBLE DATA WAREHOUSE FOR FLOW CYTOMETRY DATA

(75) Inventors: Robert Zigon, Carmel, IN (US); Larry Myers, Greenfield, IN (US); Ryan Mitchell, Brownsburg, IN (US)

(73) Assignee: Beckman Coulter, Inc., Brea, CA (US)

( * ) Notice: Subject to any disclaimer, the term of this patent is extended or adjusted under 35 U.S.C. 154(b) by 707 days.

(21) Appl. No.: 12/211,582

(22) Filed: Sep. 16, 2008

(65) Prior Publication Data

US 2010/0070459 A1 Mar. 18, 2010

(51) Int. Cl.
*G06F 17/00* (2006.01)
(52) U.S. Cl. ........................................ 707/602; 707/763
(58) Field of Classification Search .................. 715/771; 702/19, 21; 707/763
See application file for complete search history.

(56) References Cited

U.S. PATENT DOCUMENTS

| | | | |
|---|---|---|---|
| 6,606,622 B1* | 8/2003 | Sorace et al. ........................ | 1/1 |
| 7,152,073 B2 | 12/2006 | Gudbjartsson et al. | |
| 7,181,450 B2 | 2/2007 | Malloy et al. | |
| 2002/0095260 A1* | 7/2002 | Huyn .............................. | 702/19 |
| 2004/0024532 A1 | 2/2004 | Kincaid | |
| 2005/0066287 A1 | 3/2005 | Tattrie et al. | |
| 2007/0118297 A1* | 5/2007 | Thayer ............................ | 702/21 |

OTHER PUBLICATIONS

Search Report and Written Opinion mailed Oct. 23, 2009 for International Application No. PCT/US09/04077, 10 pgs.
Cavenaugh et al., "A Relational Database for Management of Flow Cytometry and ELISpot Clinical Trial Data", Cytometry Part B: Clinical Cytometry DOI, Clinical Cytometry Society, 2006, pp. 49-62.
Drakos et al., "A perspective for biomedical data integration: Design of databases for flow cytometry", BMC Bioinformatics 2008, 9:99, BioMed Central, Feb. 14, 2008, 15 pgs.

* cited by examiner

*Primary Examiner* — Belix M Ortiz Ditren
(74) *Attorney, Agent, or Firm* — K&L Gates LLP; Louis C. Cullman; Thomas A. Turano

(57) ABSTRACT

Methods, systems, and computer program products for storing, managing, querying, and displaying data are described herein. The method operates by classifying and displaying received flow cytometry data. In an embodiment, the method creates a first extensible dimension table with columns that include keywords from received data. The method creates a second extensible dimension table with columns corresponding to parameters from the received data. The method then populates dimension tables with data describing values of dimensions of the classified data. The method populates a first fact table from the classified data. The method then populates a second fact table with a summary of data from the first fact table. The method displays a user interface on a display of a computer device. The method then permits a user to select query attributes including keywords and parameters. The method builds and executes queries based upon dimensions generated from grouped selected query attributes.

14 Claims, 14 Drawing Sheets

Raw Measurements Table

| # | FS | SS | FL1 | FL2 | FL3 |
|---|---|---|---|---|---|
| 1 | 302 | 651 | 192 | 584 | 447 |
| 2 | 312 | 661 | 8 | 265 | 229 |
| 3 | 312 | 653 | 315 | 799 | 652 |
| 4 | 315 | 641 | 122 | 177 | 149 |
| 5 | 314 | 647 | 128 | 7 | 46 |
| 6 | 257 | 644 | 132 | 305 | 235 |
| 7 | 278 | 639 | 310 | 807 | 662 |
| 8 | 238 | 671 | 220 | 622 | 467 |
| 9 | 313 | 645 | 141 | 83 | 42 |

Classified Events Table 419

| # | A | B | C | D | E |
|---|---|---|---|---|---|
| 1 | + | − | + | + | − |
| 2 | + | + | − | − | + |
| 3 | − | + | + | + | + |
| 4 | − | − | − | + | − |
| 5 | + | − | − | − | + |
| 6 | + | − | + | + | − |
| 7 | − | + | − | + | + |
| 8 | + | − | − | − | + |
| 9 | + | − | + | + | − |

FIG. 4C

Statistics Table

| Stat | Count |
| --- | --- |
| A- B- | 1 |
| A- B+ | 2 |
| A+ B- | 5 |
| C+ | 1 |
| C- | 4 |
| A+ D+ E+ | 5 |
| | 0 |

Bit Vectors Table

| A | B | C | D | E | Count |
|---|---|---|---|---|-------|
| − | − | − | + | − | 1 |
| − | + | − | + | + | 1 |
| − | + | + | + | + | 1 |
| + | − | − | − | + | 2 |
| + | − | + | + | − | 3 |
| + | + | − | − | + | 1 |

EXTENSIBLE DATA WAREHOUSE FOR FLOW CYTOMETRY DATA

BACKGROUND

1. Field

The present invention is generally directed to storing and managing data in a data warehouse, and more particularly directed to storing and managing data from biological sample analyzers, such as flow cytometer instruments.

2. Background

Biological sample analyzers, such as flow cytometer instruments, are widely used for clinical and research use. A biological sample may comprise a fluid medium carrying a plurality of discrete biological particles, e.g., cells, suspended therein. Biological samples can include blood samples or other cells within a heterogeneous population of cells. Information obtained from the biological particles is often used for clinical diagnostics and/or data analyses.

Flow cytometry is a technology that is used to simultaneously measure and analyze multiple physical characteristics or dimensions of particles, such as cells. Flow cytometry includes techniques for analyzing multiple parameters or dimensions of samples. Characteristics, properties, and dimensions measurable by flow cytometry include cellular size, granularity, internal complexity, fluorescence intensity, and other features. Detectors are used to detect forward scatter, side scatter, fluorescence, etc. in order to measure various cellular properties. Cellular characteristics and properties identified by flow cytometer instruments can then be used to analyze, identify, and/or sort cells.

In traditional flow cytometry systems, a flow cytometer instrument is a hardware device used to pass a plurality of cells singularly through a beam of radiation formed by a light source, such as laser beam. A flow cytometer instrument captures light that emerges from each of the plurality of cells as each cell passes through the beam of radiation.

Currently available flow cytometry systems may include three main systems, i.e., a fluidic system, an optical system, and an electronics system. The fluidic system may be used to transport the particles in a fluid stream past the laser beam. The optical system may include the laser that illuminates the individual particles in the fluid stream, optical filters that filter the light before or after interacting with the fluid stream, and the photomultiplier tubes that detect the light beam after the light passes through the fluid stream to detect, for example, fluorescence and/or scatter. The electronic system may be used to process the signal generated by the photomultiplier tubes or other detectors, convert those signals, if necessary, into digital form, store the digital signal and/or other identification information for the cells, and generate control signals for controlling the sorting of particles. In traditional flow cytometry systems, a computer system converts signals received from light detectors into digital data that is analyzed.

Flow cytometry systems capture large amounts of data from passing thousands of cells per second through the laser beam. Captured flow cytometry data must be stored and indexed so that statistical analysis can subsequently be performed on the data. Since flow cytometers operate at very high speeds and collect large amounts of data in short amounts of time, it is necessary for the data management and storage systems to operate at very high speeds and to efficiently store and manage the data. Statistical analysis of the data can be performed by a computer system running software that generates reports on the characteristics (i.e., dimensions) of the cells, such as cellular size, complexity, phenotype, and health.

Many conventional flow cytometry systems use relational or transactional databases to store and manage the data. Relational databases are not well suited for near instantaneous analysis and display of large amounts of data. Relational databases that are traditionally used with traditional flow cytometry systems are better suited for creating records for On-Line Transaction Processing (OLTP) databases. Unlike relational databases, on-line analytical processing (OLAP) databases are designed to enhance query performance for large amounts of data (i.e., data warehouses) involving relatively few data updates (i.e., data record updates, inserts, and deletes). Although many report-writing tools exist for relational databases, query performance suffers when a large database is summarized. OLTP databases are designed to enhance data update performance, which is achieved at the expense of query performance when OLTP databases contain a large number of tables and a large amount of data. Conversely, OLAP databases allow users to alter and fine-tune query results interactively, dynamically adjusting views of the data, even in cases where the database contains large amounts of data. A design goal of OLAP databases is to enable users to form queries (i.e., ask questions) and receive results quickly. However, current OLTP and OLAP databases schemas are not dynamic in that they cannot be readily be modified or extended by users who simply request that a "new field" be created.

Traditional relational database management systems (RDBMS) are unable to provide OLAP query performance for large relational databases (i.e., databases containing more than a terabyte of data). Similarly, existing OLAP systems are not typically configured to efficiently handle large amounts of data updates.

Traditional flow cytometry database applications have focused on retrieving data from list mode files or relatively small relational OLTP databases, and are not integrated with an OLAP database or a data warehouse. Currently available flow cytometry data analysis and storage systems are limited to storage, management, and sharing of flow cytometry list mode files. Flow cytometry list mode files are files containing raw flow cytometry data, hereafter called FCS files. As used herein, a FCS file refers to flow cytometry data files compliant with the International Society for Advancement of Cytometry (ISAC) Flow Cytometry Standard (FCS). The traditional tools merely index metadata in list mode files, but do not search across hundreds, thousands, or millions of list mode files in search of past experiments that identified a particular phenotype with a particular statistical value. For example, traditional systems cannot query list mode files in search of any fact/dimension combination contained within the files. An example of a fact/dimension combination is a protocol identifying a Naïve T Cell population that occupies at least 15% of total events.

Polychromatic flow cytometry data currently includes 8 or more colors. Polychromatic flow cytometry refers to methods to analyze and display complex multi-parameter data from a flow cytometer instrument. There are technical challenges involved in analyzing and querying large amounts of Polychromatic Flow Cytometry data. In traditional systems, as flow cytometry datasets increase in size, there is a corresponding degradation in data management and query performance.

Accordingly, what is needed are methods and systems that enable storage, analysis, and mining of large amounts of Polychromatic Flow Cytometry data. Further, when list mode data files from a clinical flow cytometry lab contain patient identifiers, what is needed are systems and computer program products that are capable of unifying proteomic and genomic data alongside flow cytometry data. What is also needed are systems, methods, and computer program products that allow queried data to be modified or "cleaned up" by users in both research and clinical environments. What is further needed is a dynamically extensible database schema capable of manipulating up to 1 terabyte or more of flow cytometry data, wherein the database schema can be readily extended by users by requesting that "new fields" be created.

SUMMARY

Methods, systems, and computer program products for storing, managing, querying, and displaying data are disclosed. In an embodiment, a method for storing and managing data operates by receiving, parsing, and classifying flow cytometry data. The method parses raw event data from a flow cytometer as well as data from FCS format files. The method creates a first extensible dimension table with columns that include keywords from the raw data. The method then creates a second extensible dimension table with columns corresponding to parameters from the raw data. The method populates dimension tables that contain data describing values of dimensions of the classified data. The method then populates a first fact table from the classified data. The method populates a second fact table with a summary of the data from the first fact table. In this way, the first and second fact tables are used to store data representing the same classified data, but at a different levels of granularity.

In another embodiment of the invention, a system enables users to select query attributes and filter or constrain query results via drag and drop operations within multiple regions of a user interface. The system includes a query builder configured to generate queries based upon dimensions generated from grouped user-selected query attributes, wherein the query attributes include at least keywords and parameters. The system also includes a query executor configured to execute queries against flow cytometry data in a data warehouse which includes one or more fact tables, one or more dimension tables, and one or more extensible dimension tables. The query executor is also configured to produce results from the executed queries. The system includes an output device configured to control display of the results. In an embodiment, the system includes a filter configured to apply user-selected constraints to query results in order to produce filtered results. In an embodiment, the system includes a user interface comprising a plurality of regions, wherein the plurality regions contain command regions.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the embodiments of present invention and, together with the description, further serve to explain the principles of the invention and to enable a person skilled in the relevant art(s) to make and use the invention.

FIG. 4B depicts a raw measurements table, according to an embodiment of the invention.

FIG. 4C depicts a classified events table, according to an embodiment of the invention.

FIG. 4D depicts a statistics table, according to an embodiment of the invention.

FIG. 5B depicts a bit vectors table, according to an embodiment of the invention.

Figure 1:
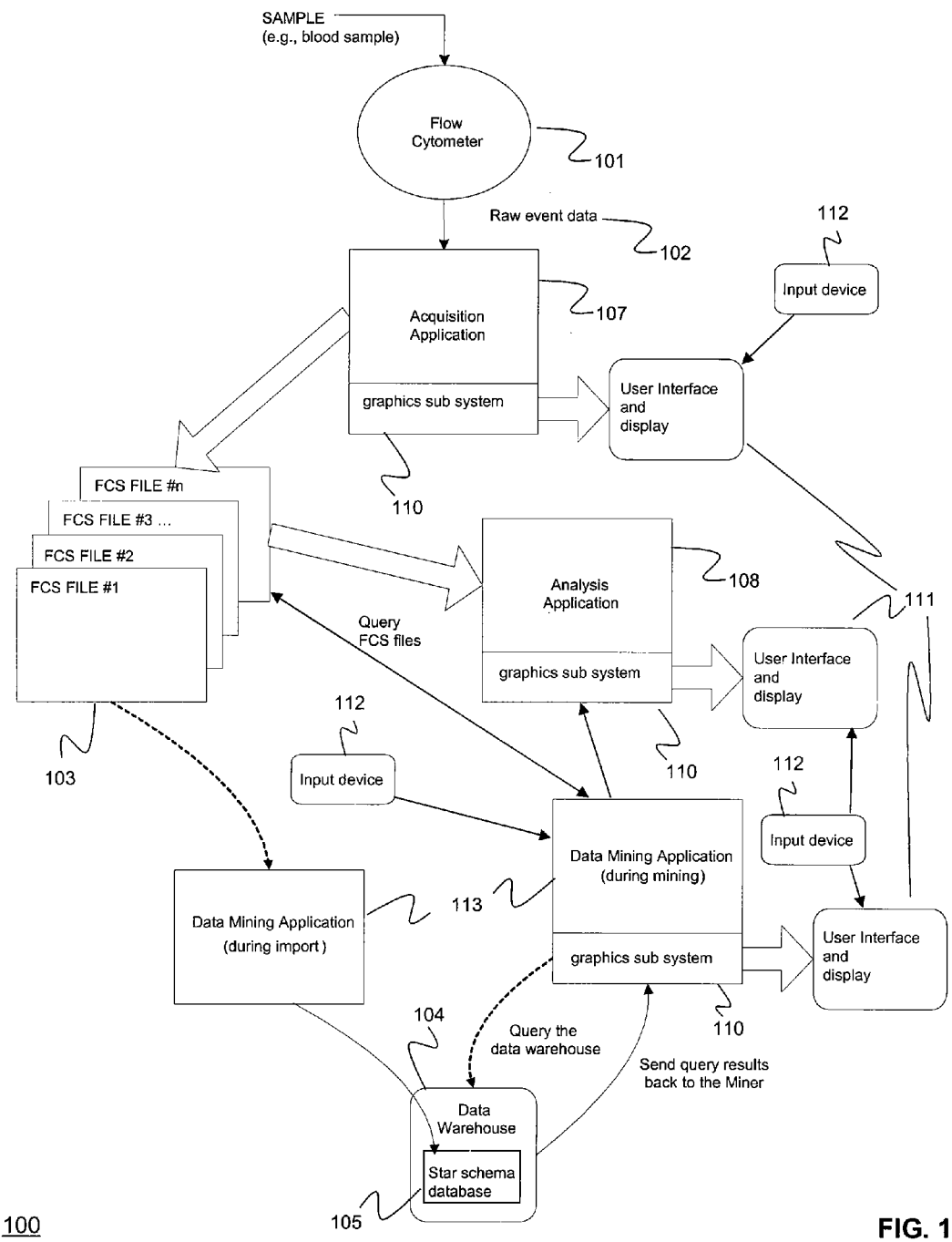
FIG. 1 illustrates the high-level diagram of a flow cytometry data management and query system, according to an embodiment of the invention.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art based on the teachings contained herein.

DETAILED DESCRIPTION

1.0 Overview of the Invention

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention disclosed herein store and manage large amounts of data from a flow cytometer instrument in an extensible data warehouse, while maintaining links to corresponding raw flow cytometry data files, thereby achieving an optimum way to organize, update, and query data in the data warehouse. Embodiments of the invention store and manage large amounts of biological sample data from flow cytometers such as hematology instruments. Versatile systems, methods, and computer program products described herein combine the desirable features of OLAP and OLTP databases, as required, while avoiding the shortcomings of each of the data management approaches. The system embodiments disclosed herein are configured to allow for dynamically extending a logical database schema as a result of user interaction with the user interface.

Embodiments of the present invention provide various methods that use data warehousing and querying techniques for biological sample analysis applications. Such methods may be used, for example, in flow cytometry systems.

The present invention includes system, method, and computer program product embodiments for storing and managing large amounts of data in a data warehouse. Embodiments of the invention include a unique extensible star schema data warehouse adaptable for use with large flow cytometry data sets.

Embodiments of the invention also include a user interface that allows users to query the data warehouse, e.g., via drag and drop operations. For example, the present invention includes system, method, and computer program product embodiments for querying and mining data in a data warehouse.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Although the present specification describes user-supplied and user-inputted data, users can be people, computer programs, software applications, software agents, macros, etc. Besides a human user who needs to access data in the data warehouse, a software application or agent sometimes needs to access data. Accordingly, unless specifically stated, the term "user" as used herein does not necessarily pertain to a human being.

Although the present specification describes the use of the MICROSOFT® SQL SERVER® Relational Database Management System (RDBMS), as would be appreciated by those skilled in the relevant art(s), the embodiments of the present invention can use other RDBMS software, such as RDBMS software available from IBM®, ORACLE®, PostgreSQL, MYSQL®, INFORMIX®, SYBASE®, and other database software vendors and distributors. Additionally, while embodiments of the present invention can run on computer platforms running various MICROSOFT® Windows operating systems capable of hosting the Microsoft's SQL SERVER® RDBMS, such as MICROSOFT® Windows XP, Mobile, Vista, and Server 2008, persons skilled in the relevant art(s) will recognize that the present invention can be implemented on computers running the UNIX®, Linux, SOLARIS®, HP-UX, Mac OS X, AIX®, and other operating systems.

Embodiments of the present invention provide systems, methods, and computer program products for managing and storing large amounts of data. For example, these embodiments are shown in FIGS. 1-5 and 7-10 below. In an embodiment, the method is used to store and manage data received from a flow cytometer instrument. According to an embodiment, the method creates a first extensible dimension table with columns that include keywords from data received from a flow cytometer. The method then creates a second extensible dimension table with columns corresponding to parameters from the received flow cytometry data. The method populates dimension tables that contain data describing values of dimensions of the classified data. The method then populates a first fact table from the classified data. The method populates a second fact table with a summary of the data from the first fact table. Embodiments of the invention allow users to search across hundreds, thousands, or millions of flow cytometry list mode files which include data from past experiments that identified a particular phenotype.

In another embodiment, a system that builds database queries based upon graphically-selected query attributes and constraints is presented. For example, these embodiments are shown in FIGS. 1, 2, and 7-10 below. The system in this embodiment includes a graphical user interface (GUI) that enables users to select query attributes, and filter or constrain the results via drag-and-drop operations within multiple regions or windows of the GUI. A first region of the interface displays flow cytometry attributes. The attributes may include keywords found within FCS files. The system groups attributes into classes known as dimensions. Attributes can include one or more of Calendar, Datasets, Equipment, and Keyword dimensions. The system then generates and displays reports in a second window after users select an attribute and drag it to the report region of the interface. The system applies constraints to queries (i.e., string searches, logic operations, Boolean operations, etc.) when a user selects a value for one or more constraints in a third region of the interface. When a user drags an attribute from the attributes window to the constraints window and picks a value to constrain on, the system filters the rows displayed in the report window. In response to user input (i.e., dragging an attribute from the attributes panel and selecting one or more constraints in the constraints window), the system generates queries that are subsequently executed against a data warehouse. The system graphically depicts raw flow cytometry data from FCS files that have been correlated to database records displayed in the report window. In one embodiment, the FCS files are correlated to database records displayed in the report window based on sample identifiers within the data. When a record in the report area is selected, the system extracts and displays dot plots and histograms from the corresponding FCS files, which are displayed in a fourth window.

1.1 Components of the Data Management System

Figure 8:
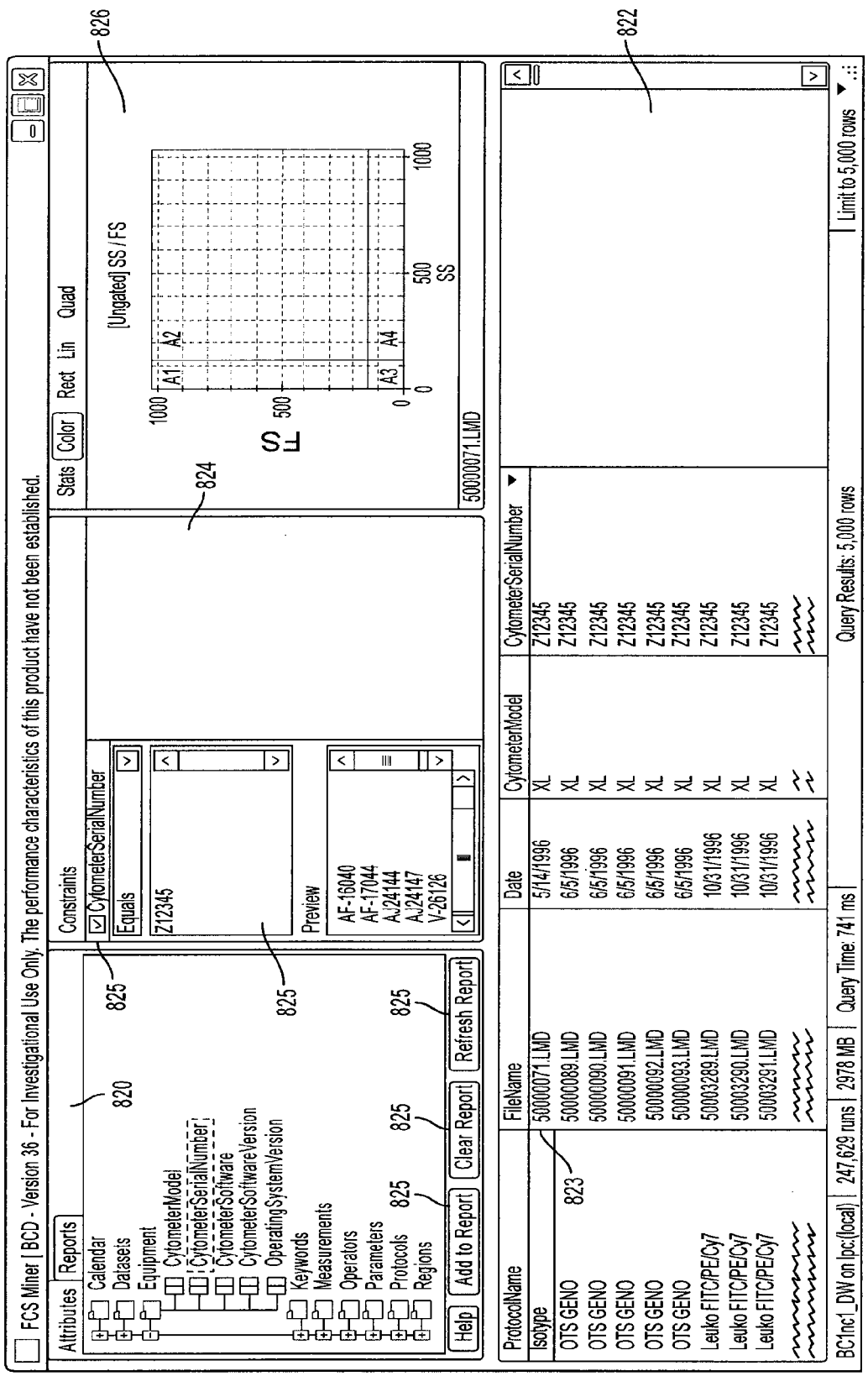
FIGS. 8 and 9 depict a graphical user interface (GUI) for a data mining system, according to an embodiment of the invention.
Figure 9:
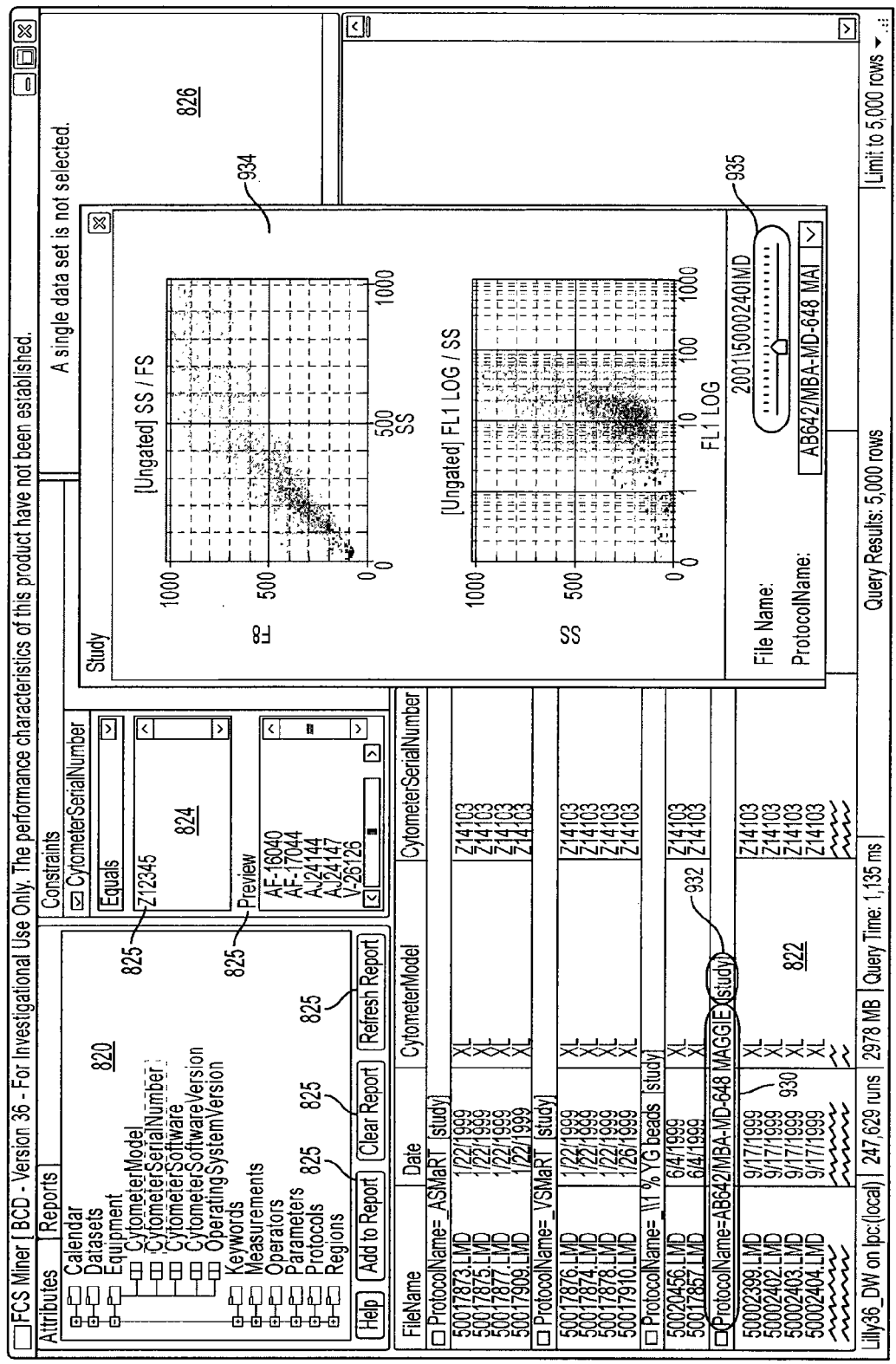

FIG. 1 illustrates a flow cytometry data management and query system 100, in accordance with an embodiment of the invention. System 100 includes a flow cytometer 101, FCS files 103, a data warehouse 104 including a star schema database 105, an acquisition application 107, an analysis application 108 including a graphics sub-system 110, a user interface 111, and a data mining application 113 (e.g., data miner or data import device). An exemplary detailed view of user interface 111 is shown in FIGS. 8 and 9, discussed in Section 4.1 below.

Data warehouse 104 can be used to store and manage raw event data 102 received either from flow cytometer 101 or acquisition device 107. In an embodiment, raw event data 102 is stored in FCS files 103 and summarized data, processed using data mining device 113, is written to a star schema database 105. In an embodiment, FCS files 103 are related or linked to summary data in database tables within star schema database 105 by sample identifiers. For example, the sample identifiers may be patient identifiers or another unique identifier within FCS files 103.

User interface 111 can allow users, such as clinicians and scientists, to choose which FCS files 103 to store in data warehouse 104.

Data mining device 113 can allow users to control, via user interface 111, which FCS files 103 to be stored in data warehouse 104. Data mining device 113 can also allow a user to build and execute queries against data stored within data warehouse 104. Query results can be returned from data warehouse 104 and displayed on user interface 111 under control of data mining device 113.

Figure 2:
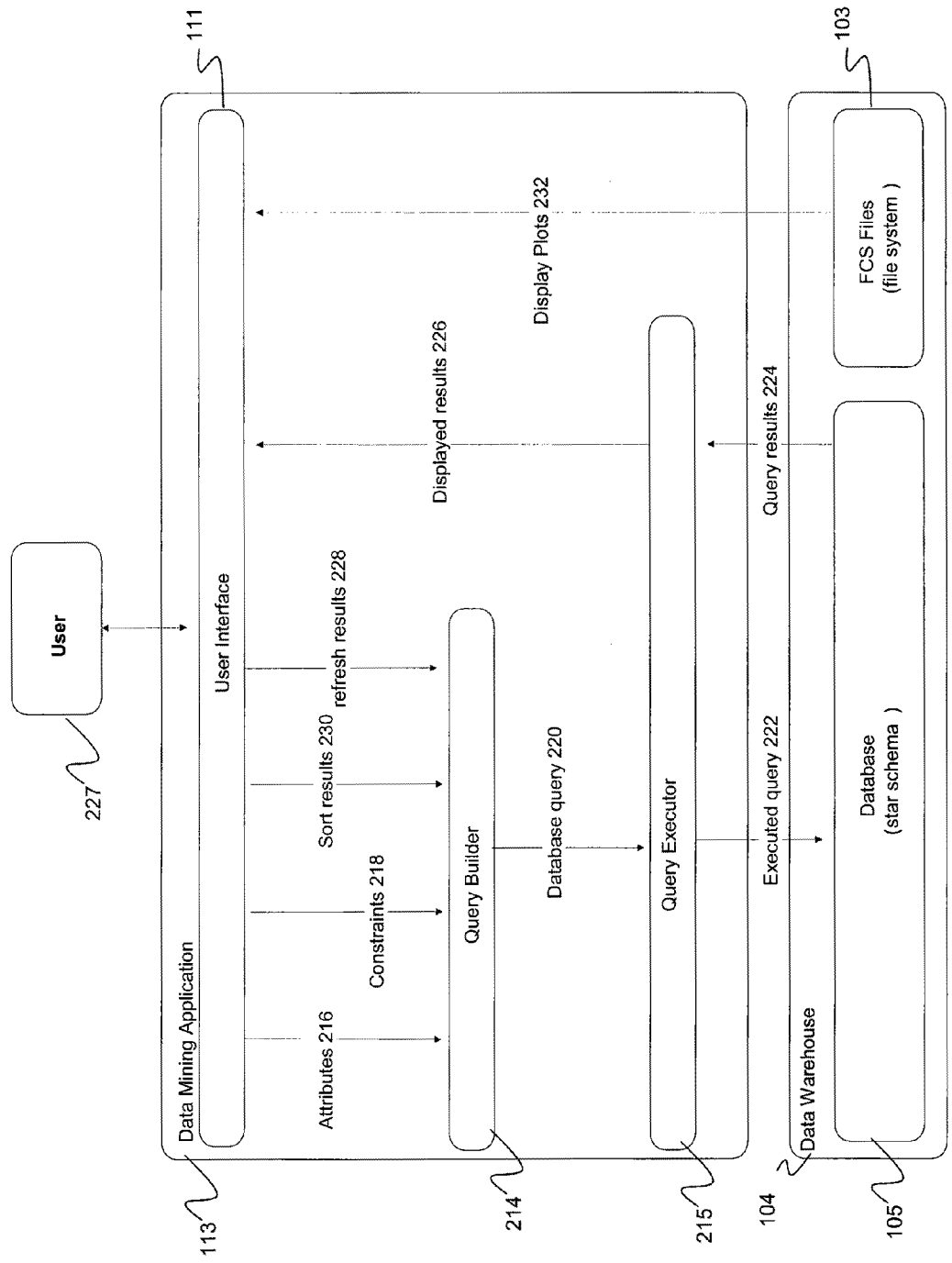
FIG. 2 depicts data flow between components of a data management and query system, in accordance with an embodiment of the invention.

FIG. 2 illustrates data flow 200 between components of data mining device 113 and data warehouse 104, according to an embodiment of the present invention. In the embodiment of FIG. 2, data mining device 113 includes a query builder 214, which is coupled to user interface 111, and a query executor 215, which is coupled between query builder 214 and data warehouse 104.

In the example shown, data flow 200 occurs between user interface 111 and components of data mining device 113. An exemplary detailed view of the data flow is shown in FIGS. 8 and 9, discussed below. In an embodiment, user interface 111 allows a user 227 to select query attributes 216 to be used by query builder 214 to generate database queries 220. For example, as discussed below with respect to FIGS. 8 and 9, user interface 111 allows user 227 to query database 105 by interacting with attributes 216. User interface 111 also allows user 227 to filter out data according to selected constraints 218, which are also used by query builder 214. For example, user interface 111 allows user 227 to change queries 220 built by query builder 214 by interacting with constraints 218. According to an embodiment, user 227 uses an input device (not shown), for example, but not limited to, a pointing device, a track ball, a touch pad, a joy stick, a voice activated control system, rotary dials, a touch screen, or the like to select query attributes 216 and constraints 218.

Query builder 214 generates database queries 220 based upon selections made in user interface 111 by user 227. In an embodiment, query builder 214 can be configured to generate queries 220 based upon dimensions generated from grouped user-selected query attributes 216, wherein query attributes 216 include at least keywords and parameters.

According to an embodiment, query executor 215 receives database queries 220 from query builder 214. Query executor 215 is configured to execute database queries 222 against data in data warehouse 104 and to return the corresponding query results 224, which displayed results 226 are displayed in user interface 111. In an embodiment, user interface 111 is an output device configured to control displaying of displayed query results 226 to user 227. Query builder 214 may also be configured to apply constraints 218 selected by user 227 in user interface 111. For example, constraints 218 selected using user interface 111 can be applied to returned results 226 displayed by query executor 215 in user interface 111 to produce filtered results.

Additionally, or alternatively, as shown in FIG. 2, user 227 can submit a request to sort results 230 or refresh results 228 via user interface 111 to query builder 214. For example, when a refresh request 228 is received by query builder 214, an existing, stored query 220 is re-run by query executor 215. Similarly, when a sort request 230 is received by query builder 214, an existing query 220 is modified and submitted to query executor 215. In an embodiment, query builder 214 is configured to build write queries in the structured query language (SQL). For example, when a sort request 230 is received, query builder 214 may alter an existing SQL query to add or alter one or more 'ORDER BY' clauses to effectuate the user-selected results sorting.

User interface 111 is configured to control the graphical depiction of data from FCS files 103 a display plots signal 232. For example, scatter plots, histograms, hierarchical tree plots, star coordinate plots, and the like, corresponding to subpopulations of data within FCS files 103 can be displayed on user interface 111 based upon user 227 using the input device to select results in user interface 111.

2.0 Schema of the Data Warehouse

Figure 3:
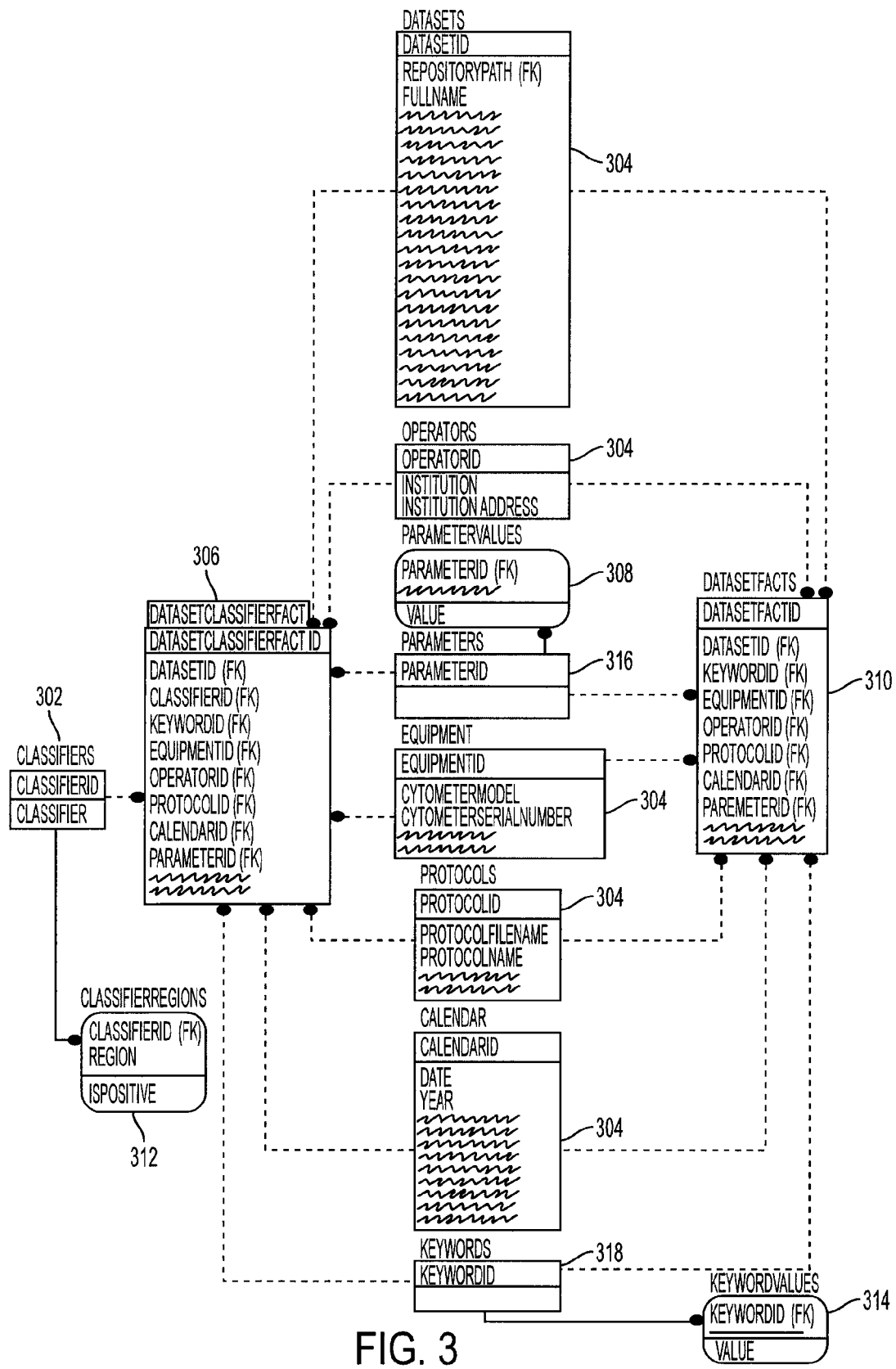
FIG. 3 depicts an extensible, dual star schema database, in accordance with an embodiment of the invention.

FIG. 3 illustrates data warehouse schema 300, in accordance with an embodiment of the invention. Schema 300 includes Classifier(s) table(s) 302, a dimension table(s) 304 (e.g., Datasets, Operators, Equipment, Protocols, Calendar, etc.), a fact table(s) 306, parameter(s)/value(s) table(s) 308 (e.g., an extensible dimension table), a DatasetFact(s) table(s) 310, a ClassifierRegion(s) table(s) 312 (e.g., an extensible dimension table), keyword(s)/value(s) table(s) 314 (e.g., an extensible dimension table), a parameters table(s) 316, and a keyword(s) table(s) 318. Schema 300 is configured as a two "stars" schema. A first star is organized around fact table 306 and a second star is configured around DatasetFact table 310. Embodiments of the present invention can include a data warehouse schema 300 comprising three or more stars organized around three or more fact tables (not depicted in FIG. 3).

In accordance with an embodiment of the invention, fact table 306 includes one or more foreign keys, which are designated as "(FK)" in FIG. 3. As used herein a foreign key is a referential constraint between two tables in star schema database 105 (FIGS. 1-2). A foreign key identifies a column or a set of columns in a referencing table that refers to a column or set of columns in a second, referenced table. In the example embodiment depicted in FIG. 3, the ParameterID column in fact table 306 refers to the ParameterID column in the referenced Parameters table 316. Similarly, the EquipmentID column in fact table 306 refers to the EquipmentID column in dimension table 304 (e.g., the Equipment table in the specific embodiment depicted in FIG. 3). The foreign key columns in a referencing table, such as fact table 306, must be either part of a primary key or another unique key in the referenced table(s). Primary keys are discussed in greater detail below. The values in one row of the referencing columns must occur in a single row in the referenced table, such as the Equipment table. Thus, a row in the referencing table cannot contain foreign key values that do not exist in the referenced table. In this way, references are made that link data together between fact table 306, dimension table(s) 304, parameters table 316, and other tables in star schema database 300. For example, fact table 306 is linked or related to extensible dimension table 312 via the foreign key on the ClassifierID column, which is a unique or primary key for the first extensible dimension table (the ClassifierRegions table in the specific embodiment depicted in FIG. 3).

As would be understood by those skilled in the relevant art, primary keys may also be defined for tables in star schema database 105 (FIG. 1), wherein the primary keys uniquely identify each row in each of the respective tables. Each table in star schema database 105 may have at most one primary key, wherein the primary key comprise one or more columns, provided that no two distinct rows in the table has the same value (or combination of values) in those columns. For example, in the embodiment depicted in FIG. 3, the ParameterID column is part of the primary key for ParameterValues table 308 and the combination of values stored in the Parameter and ParameterID columns are unique within ParameterValues table 308. The ParameterID column is also a foreign key referencing Parameters table 316 and fact table 306. Note that tables in star schema database 105 or 300 may also have one or more unique keys in addition to a primary key.

In an embodiment, the first star of schema 300 is queried when a user generates queries involving phenotypic classifiers. Fact table 306 is populated with a summary of classified data including phenotypic classifiers, and fact table 310 is populated with a summary of the classified data lacking phenotypic classifiers.

As noted above, schema 300 also includes the second star, which is organized around fact table 310. In the specific embodiment illustrated in FIG. 3, fact table 310 is the DatasetFacts table, which incorporates attributes from the Datasets, Operators, Parameters, Equipment, Protocols, Calendar, and Keywords dimensions. In an embodiment, the second star is queried when a user generates questions or queries that do not involve the phenotypic classifiers.

According to an embodiment, the number of rows in fact table 310 is approximately 1/30th of the row count in fact table 306. This is desired because this reduced table size for fact table 310 results in queries that run approximately 10 times faster than when fact table 306 is accessed.

In the embodiment depicted in FIG. 3, fact table 306 is the DatasetClassifierFact table and fact table 310 is the DatasetFacts table.

Dimension table(s) 304 can contain data that describe values of dimensions of the classified data stored in fact table 306 and fact table 310. As depicted in FIG. 3, dimension table(s) 304 can include data related to Datasets, Operators, Equipment, Protocols, and Calendar dimensions.

Additionally, or alternatively, schema 300 allows for extensibility. For example, schema 300 includes a first extensible dimension table 314, which includes columns having keywords associated with fact table 306. Extensible dimension table 314 can be a KeywordValues table with KeywordID, Keyword, and Value columns. Extensible dimension table 314 can be a collection of name value pairs.

In one example, when a query against one of the two stars in schema 300 accesses Keywords table 318, the KeywordValues table is pivoted to create a view that essentially has a variable number of columns. The pivot operation is described in further detail in Section 3.0 below.

In the example shown, schema 300 also includes a second extensible dimension table 308 used to store parameters associated with fact table 310. Second extensible dimension table 308 can be the ParameterValues table with ParameterID, Parameter, and Value columns.

In accordance with an embodiment of the invention, schema 300 further includes a third extensible dimension table 312 that includes columns having region identifiers associated with fact table 306. In the example embodiment depicted in FIG. 3, the third extensible dimension table 312 is the ClassifierRegions table which includes a Region column that identifies regions used to classify event data.

As the number of cytometry parameters that will be used in a protocol cannot be readily predicted, according to an embodiment, the ParameterValues table 308, like the KeywordValues table 314, is an extensible dimension table that is pivoted to create a variable number of columns. The pivoting operation is discussed in greater detail below in Section 3.0 with reference to populating data warehouse 104.

3.0 Populating the Data Warehouse

With reference to FIGS. 1 and 3 above, according to an embodiment of the present invention, data is imported into data warehouse 104 by storing a collection of keyword/value pairs. In an embodiment, the keyword/value pairs used to populate database tables within data warehouse 104 are parsed from raw event data 102 from flow cytometer instrument 101 depicted in FIG. 1. In another embodiment, the keyword/value pairs used to populate tables in data warehouse 104 are parsed from FCS files 103. In accordance with an embodiment of the present invention, more than 250,000 FCS files 103 comprising in excess of 200 GB of flow cytometry data can populate tables in star schema database 105. In an embodiment, received raw event data 102 is parsed to determine if it contains phenotypic classifiers. The phenotypic classifiers are used to populate first fact table 306. The set of possible keywords found within FCS files 103, raw event data 102, or other data used to populate data warehouse 104 is not known. For example, each FCS file 103 may contain its own custom keywords. These custom keywords may be defined by users, provided they comply with the ISAC FCS standard. Table 1 below depicts an approach to populating the data warehouse 104 with keyword data, in accordance with an embodiment of the invention.

TABLE 1

| Raw FCS Data (one row per FCS file) | | | | | | | |
|---|---|---|---|---|---|---|---|
| FILE_ID | SAMPLE_ID | INSTITUTION | SERIAL_NO | OPERATOR | EXPERIMENT | CUSTOM1 | CUSTOM2 |
| 1 | 100 | Community | BC10101 | John Doe | Experiment1 | {not provided} | DEF |
| 2 | 105 | Methodist | BC20202 | Jane Smith | {not provided} | ABC | {not provided} |
| 3 | 110 | Methodist | BC20202 | {not provided} | {not provided} | {not provided} | {not provided} |
| 4 | 100 | Community | BC10101 | John Doe | Experiment1 | {not provided} | DEF |
| 5 | 100 | Community | BC10101 | John Doe | Experiment1 | {not provided} | DEF |

In order to reduce query execution times and data storage requirements, it is advantageous to eliminate data redundancy. Query performance against sparsely populated tables, such as the raw FCS data Table 1 depicted above, is degraded due to the need to scan data rows that contain either no data (indicated as "{not provided}" in Table 1 above) or redundant data. The first step to eliminating redundancy is to reduce the size of the raw FCS data table (Table 1). To accomplish this, Table 1 is scanned to remove duplicate rows. After making a pass over Table 1, a new table, Table 2, is populated with the unique rows.

TABLE 2

Unique Keyword Combinations

| KEYWORD_ID | SAMPLE_ID | INSTITUTION | SERIAL_NO | OPERATOR | EXPERIMENT | CUSTOM1 | CUSTOM2 |
|---|---|---|---|---|---|---|---|
| 1 | 100 | Community | BC10101 | John Doe | Experiment1 | {not provided} | DEF |
| 2 | 105 | Methodist | BC20202 | Jane Smith | {not provided} | ABC | {not provided} |
| 3 | 110 | Methodist | BC20202 | {not provided} | {not provided} | {not provided} | {not provided} |

After Table 2 is created and populated, a mapping between the unique keyword combinations stored within Table 2 and the corresponding recordings representing raw FCS data files in Table 1 is generated. This mapping from FCS files (Table 1) to unique FCS keyword combinations (Table 2) is stored in a third table, Table 3 depicted below. In accordance with an embodiment of the invention, the mapping is stored in one or more dimension tables 304 depicted in FIG. 3. For example, fact table 310 may be DatasetFacts depicted in FIG. 3. As listed in Table 3 below, the file ID (DatasetID) of Table 1 is associated with the unique FCS combination (KeywordID) of Table 2.

TABLE 3

Map Files to Keywords

| FILE_ID | KEYWORD_ID |
|---|---|
| 1 | 1 |
| 2 | 2 |
| 3 | 3 |
| 4 | 1 |
| 5 | 1 |

In one example, a complete set of keywords is not readily known, and as the keyword set can change dynamically as a result of user actions, the complete set of keywords may not ever be fully defined. One solution for this is to add database table columns to a database schema at query runtime. However, this solution may have some drawbacks for datasets containing a large set of keywords, including, but not limited to, flow cytometry data. However, embodiments of the present invention allow for effective query performance when large numbers of keywords are involved. Additionally, as there may be hundreds of unique keyword names, the traditional method of adding columns to a database schema results in tables containing too many columns (i.e., exceeding the maximum number of columns supported by many database management systems). In accordance with an embodiment of the present invention, a solution to this problem is to "fold" (or "unpivot") the data. For example, folding the data rotates columns of a database table into database column values. Table 4 below illustrates the folded representation of Table 2 above, wherein columns of Table 2 are stored as column values within rows of Table 4.

TABLE 4

Folded FCS Keywords

| KEYWORD_ID | KEYWORD | VALUE |
|---|---|---|
| 1 | SAMPLE_ID | 100 |
| 1 | INSTITUTION | Community |

TABLE 4-continued

Folded FCS Keywords

| KEYWORD_ID | KEYWORD | VALUE |
|---|---|---|
| 1 | SERIAL_NO | BC10101 |
| 1 | OPERATOR | John Doe |
| 1 | EXPERIMENT | Experiment1 |
| 1 | CUSTOM1 | {not provided} |
| 1 | CUSTOM2 | DEF |
| 2 | SAMPLE_ID | 105 |
| 2 | INSTITUTION | Methodist |
| 2 | SERIAL_NO | BC20202 |
| 2 | OPERATOR | Jane Smith |
| 2 | EXPERIMENT | {not provided} |
| 2 | CUSTOM1 | ABC |
| 2 | CUSTOM2 | {not provided} |
| 3 | SAMPLE_ID | 110 |
| 3 | INSTITUTION | Methodist |
| 3 | SERIAL_NO | BC20202 |
| 3 | OPERATOR | {not provided} |
| 3 | EXPERIMENT | {not provided} |
| 3 | CUSTOM1 | {not provided} |
| 3 | CUSTOM2 | {not provided} |

In a database of significant size and variety, there will be a large number of unpopulated values (depicted as "{not provided}" in Tables 1, 2, and 4 above). In some cases, query and data update performance may be diminished in databases comprised of tables with large numbers of unpopulated or sparsely populated columns because these columns must be scanned and indexed. As used herein, an unpopulated column in a table is equivalent to a column containing a null value. In the folded Table 4, these null values are additional data that does not add useful information and results in longer query times. As the null columns may not be useful, an embodiment of the present invention filters null columns out and produces a new table, Table 5, as illustrated below.

TABLE 5

Folded Keywords Without NULL Values

| KEYWORD_ID | KEYWORD | VALUE |
|---|---|---|
| 1 | SAMPLE_ID | 100 |
| 1 | INSTITUTION | Community |

TABLE 5-continued

Folded Keywords Without NULL Values

| KEYWORD_ID | KEYWORD | VALUE |
|---|---|---|
| 1 | SERIAL_NO | BC10101 |
| 1 | OPERATOR | John Doe |
| 1 | EXPERIMENT | Experiment1 |
| 1 | CUSTOM2 | DEF |
| 2 | SAMPLE_ID | 105 |
| 2 | INSTITUTION | Methodist |
| 2 | SERIAL_NO | BC20202 |
| 2 | OPERATOR | Jane Smith |
| 2 | CUSTOM1 | ABC |
| 3 | SAMPLE_ID | 110 |
| 3 | INSTITUTION | Methodist |
| 3 | SERIAL_NO | BC20202 |

Table 5 is an example of the extensible dimension table 314 depicted in FIG. 3, and is part of dual-star database schema 300. According to an embodiment of the invention, Table 5 is implemented as the extensible KeywordValues table. In an embodiment, the extensible Keywords table is used to generate KeywordID values and to enforce referential integrity against other tables containing KeywordID columns, but queries are not run directly against extensible dimension table 318.

In accordance with an embodiment of the present invention, a database pivot operation enables a clinician, scientist, or other user, to change the dimensional orientation of query results, report, or page displayed on user interface 111 depicted in FIGS. 1 and 2. For example, data in star schema database 105 can be viewed in various ways, such as displaying data from one dimension table 304 "down" a page of user interface 111 and data from a second dimension table 304 "across" a page of user interface 111. The displayed data can encompass a specified time period, patient (uniquely identified by a patient identifier), type of sample (i.e., blood), etc.

In one embodiment, after viewing the data in a first arrangement, the clinician or user can then immediately view the data in a second arrangement with a subsequent pivot operation. The displayed data can be re-oriented so that the data displayed has data from the second dimension table 304 "across" the page and data from the first dimension table 304 "down" the page of user interface 111. This second, pivoted view of the data is generated efficiently; therefore the clinicians and scientists do not have to wait a significant amount of time for results to be displayed on user interface 111. According to embodiments of the present invention, the pivot operation can be performed nearly instantaneously (e.g., within seconds), which represents a performance advantage over traditional relational and OLTP databases which require much longer query execution times in order to produce similar query results.

In an embodiment of the invention, Microsoft SQL Server's PIVOT operator is used in order to perform the pivot operations by issuing queries against folded Table 5. Although an embodiment of the invention uses the PIVOT operator implemented in Microsoft SQL Server 2005, as would be appreciated by those skilled in the relevant art, the present invention can use other database management software that implements similar pivot operations. In accordance with an embodiment depicted in FIG. 3, the query syntax is similar to the SQL statement below:

```
SELECT ... FROM ... left outer join KeywordValues pivot
(max(Value) for Keyword in (SAMPLE_ID, INSTITUTION,
SERIAL_NO, OPERATOR, EXPERIMENT, CUSTOM1,
CUSTOM2)) KeywordValues on
[DatasetClassifierFacts].KeywordID =
KeywordValues.KeywordID WHERE ...<query
conditions/constraints>;
```

As illustrated by the SQL statement above, the columns to pivot can be specified as part of the query. While this may complicate query generation, it increases query execution speed by reducing the time needed for the query to complete and return results from second extensible dimension table 314. This "pivot" operation also enables an embodiment of the invention to manipulate in excess of 1 terabyte of flow cytometry data. Due to the ad-hoc nature of the queries to be run against the data warehouse 104, embodiments of the present invention provide the infrastructure for a complex query builder 214 capable of generating queries that perform pivot operations against the data warehouse 104 disclosed herein.

Figure 4A:
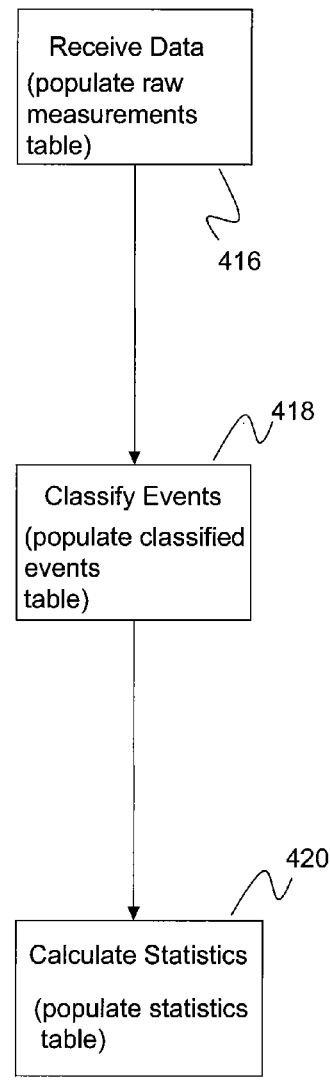
FIG. 4A is a flowchart representing a method for populating a data warehouse, according to an embodiment of the invention.

FIG. 4A is a flowchart depicting a method 400 illustrating the steps (416, 418, and 420) by which raw data is classified and stored in a data warehouse, in accordance with an embodiment of the present invention. FIGS. 4B, 4C, and 4D illustrate exemplary tables 417, 419, and 422, respectively, populated during one or more of the steps depicted in FIG. 4A. For example, the flowchart in FIG. 4A depicts a method 400 and illustrates the steps by which data warehouse 104 is populated with received data. Method 400 is described with reference to the embodiments of FIGS. 1-3. However, method 400 is not limited to those example embodiments. Note that the steps in the flowchart do not necessarily have to occur in the order shown.

The method begins at step 416, where received data is parsed, and a raw measurements table (e.g., Raw Measurements Table 417 in FIG. 4B) is populated. In accordance with embodiments of the invention, the type of data received in step 416 can be raw event data 102 acquired by acquisition software, data from an FCS file 103, or the like. According to an embodiment of the present invention, the received data is parsed in step 416 to determine if the data contains phenotypic classifiers. In an embodiment, the received data is also parsed in step 416 to determine if a sample identifier is in the received data, and the sample identifier is used to populate at least one dimension table in star schema database 105. According to embodiment of the invention, the sample identifier may be a patient identifier or another unique identifier in the received data. In one embodiment, raw measurements table 417 is stored within star schema database 105 (although table 417 is not depicted in FIG. 3).

According to an embodiment, the received data is parsed in step 416 to determine if there is proteomic data in the received data, and star schema database 105 is populated such that patient identifier is correlated to proteomic data from cytometer 101. As used herein, proteomic data refers to data representing a complement of proteins contained with the received data, including any modifications made to a particular set of proteins, wherein the proteins are produced by organisms or systems. In an embodiment of the invention, the parsing in step 416 determines if the received data contains genomic data, and star schema database 105 is populated, such that flow cytometry data is related to genomic data based upon the patient identifier. As used herein, genomic data refers to data representing an organism's genome, including, but not limited to, hereditary information encoded in Deoxyribonucleic acid (DNA) and Ribonucleic acid (RNA).

In the example embodiment depicted in FIGS. 4B and/or 4C, there are 9 events. The events data is parsed in step 416 and is used to populate raw measurements table 417. Each row in raw measurements table 417 represents an event. According to an embodiment, each event is numbered sequentially and there are 5 parameters, wherein each parameter is represented by a column in raw measurements table 417. In the embodiment depicted in FIG. 4B, the 5 parameters are FS, SS, FL1, FL2, and FL3. In accordance with an embodiment of the present invention, an amount of time needed for parsing a large set of received data increases only incrementally as raw event data 102 is acquired from flow cytometer instrument 101. This is an advantage over traditional methods and systems wherein the amount of time needed to parse large amounts of received data is based on parsing an entire set of data from a flow cytometer. After raw measurements table 417 is populated with received data, method 400 moves to step 418.

In step 418, the received data is classified and classified events table 419, depicted in FIG. 4C, is populated. In an embodiment of the present invention, analysis software is used to perform gating of the received data. For example, gates may be created by a user. Gates may also be automatically generated using a clustering algorithm. In the example embodiment depicted in FIG. 4C, the raw measurements have been classified by 5 gates. In the specific embodiment illustrated in FIG. 4C, each gate is represented by a column in classified events table 419, and the gates are named A, B, C, D, and E. In the embodiment depicted in FIG. 4C, an event stored within classified events table 419 is either inside a gate (positive) or outside of the gate (negative). For example, event 1 in classified events table 419 is inside gates A, C, and D and is outside gates B and E as indicated by the positive and negative values stored in classified events table 419. For example, event 1 can be represented by a record in classified events table 419 as A+ (A positive), or B− (B negative).

In step 420, statistics are determined or calculated for the classified data in classified events table 419, and statistics table 422 in FIG. 4D is populated. In an embodiment, summary statistics are computed by totaling the classified events stored in classified events table 419. According to an embodiment of the invention, a user, such as a clinician or scientist, performs step 420 by selecting statistics that are of interest for a current experiment. In one example, statistics table 422 is stored within star schema database 105 (FIG. 1, but table 422 is not depicted in FIG. 3).

In the example embodiment depicted in FIG. 4D, A+B− has an event count of 5 as there are 5 classified events that are both A positive and B negative (e.g., events 1, 5, 6, 8, and 9 stored in classified events table 419).

Figure 5A:
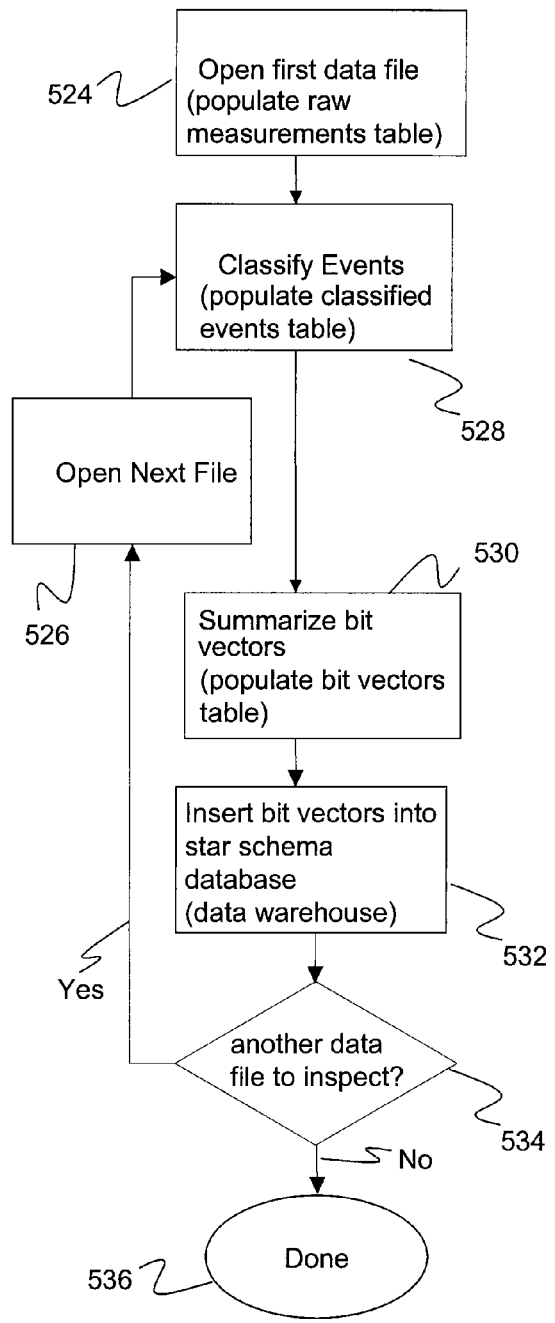
FIG. 5A is a flowchart representing a method for populating a star schema database, according to an embodiment of the invention.
Figure 5B:
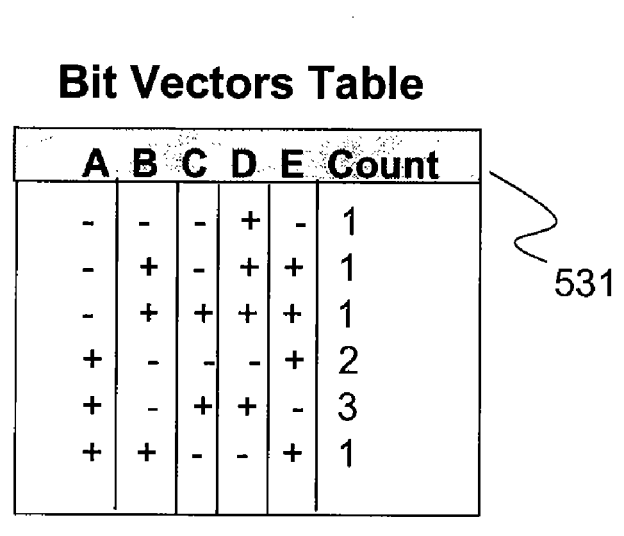

FIG. 5A is a flowchart depicting a method 500 illustrating steps (524-530 and 532-536) by which a database is populated, according to an embodiment of the invention. FIG. 5B shows an exemplary table 531, for example a Bit Vectors Table, populated from method 500.

More particularly, method 500 illustrates the steps by which star schema database 105 (FIG. 1) is populated with data from one or more data files. Method 500 is described with reference to the embodiments of FIGS. 1-4. However, method 500 is not limited to those example embodiments. Note that the steps in method 500 do not necessarily have to occur in the order shown.

The method begins at step 524, where a first data file is opened, the data file is scanned, and a raw measurements table, e.g., table 417 in FIG. 4B, is populated. In accordance with an embodiment of the present invention, the first data file can comprise raw event data 102. The first data file can also be an FCS file 103. As depicted in FIGS. 1 and/or 2, an embodiment of the invention includes a user interface that allows a user to select which FCS file(s) 103 the user wants to use to populate data warehouse 104. In step 524, the first data file is parsed and raw measurements table 417 is populated, similar to as described above in step 416 of method 400. In accordance with an embodiment of the invention, the data file is parsed in step 524 to determine if the data contains phenotypic classifiers. According to another embodiment, the data file is also parsed to determine if a patient identifier is in the data file, and the patient identifier is used to populate at least one table in star schema database 105. In a further embodiment, the data file is also parsed to determine if there is proteomic data in the data file. If so, star schema database 105 is populated, such that patient identifiers are related to proteomic data that represents the complement of proteins contained with the data file. In step 524, FCS files 103 are scanned as raw event data 102 is written to FCS files 103. In this way, the resources needed to scan a large number of FCS files 103 are used incrementally as raw event data 102 is written to FCS files 103 (i.e., the costs associated with scanning FCS files 103 are paid incrementally). After the first data file is used to populate raw measurements table 417, method 500 moves to step 528.

In step 528, events are classified. For example, classified events table 419 in FIG. 4C can be populated with the classified events. In one example, classified events table 419 is populated as described above in step 418 of method 400. After classified events table 419 is populated, method 500 moves to step 530.

In step 530, bit vectors are summarized. In one example, the summarized bit vectors are used to populate bit vector table 531 in FIG. 5B. According to an embodiment of the invention, bit vector table 531 is populated with counts representing the number of unique bit vectors within data from the data file. In other words, bit vector summary table 531 counts the number of unique bit vectors within the data. In one example, this aggregated data is stored in star schema database 105. In step 530, data can be aggregated in order to reduce the data to a maximum of $2^n$ values, where n is the number of gates. As discussed above in the description of step 418 of method 400, gates may be associated with a displaying of a plot of the received data by user 227. Gates may also be automatically generated using a clustering algorithm. For example, when there are 5 gates, there are 32 possible bit vectors. When there are a large number of gates, the corresponding number of bit vectors grows. For example, when there are 16 gates, 65,536 bit vectors are populated in bit vector table 531. As would be understood by those skilled in the relevant art(s), it is time-intensive to parse a large set of raw event data 102 in order to populate a database such as star schema database 105. Similarly, it can be time-intensive to scan multiple data files, such as FCS files 103, in order to populate star schema database 105 used in data warehouse 104. Therefore, using method 500, vectors are only stored in bit vector table 531 if it contains one or more events (its count is greater than zero). This can be desirable as this operation decreases data storage requirements (i.e., less disk space is consumed), increases the speed of data storage, and increases query performance. Typically only a small number of bit vectors contain events. In the worst case, there may not be more bit vectors than there are events in the data file opened in step 524. After bit vector table 531 is populated, method 500 moves to step 532.

In step 532, bit vectors are inserted into star schema database 105 within data warehouse 104, method 500 moves to step 534.

In step 534, a determination is made regarding whether another data file is available to inspect. In one example, step 534 is performed by monitoring for subsequent received data files. In an embodiment, step 534 involves determining if an FCS file 103 has been received after the first data file was opened in step 524. If it is determined in step 534 that a data file has been received subsequent to step 524, method 700 moves to step 526. If it is determined in step 534 that no other data files have been received, method 500 moves to step 536 where the process ends.

If data has been received subsequent to step 524, in step 526 the next data file is opened. According to an embodiment, the next data file is an FCS file 103. After the next data file is opened, method 700 moves to step 528, and steps 528-530 and 532-536 are repeated.

4.0 Data Mining

Figure 6:
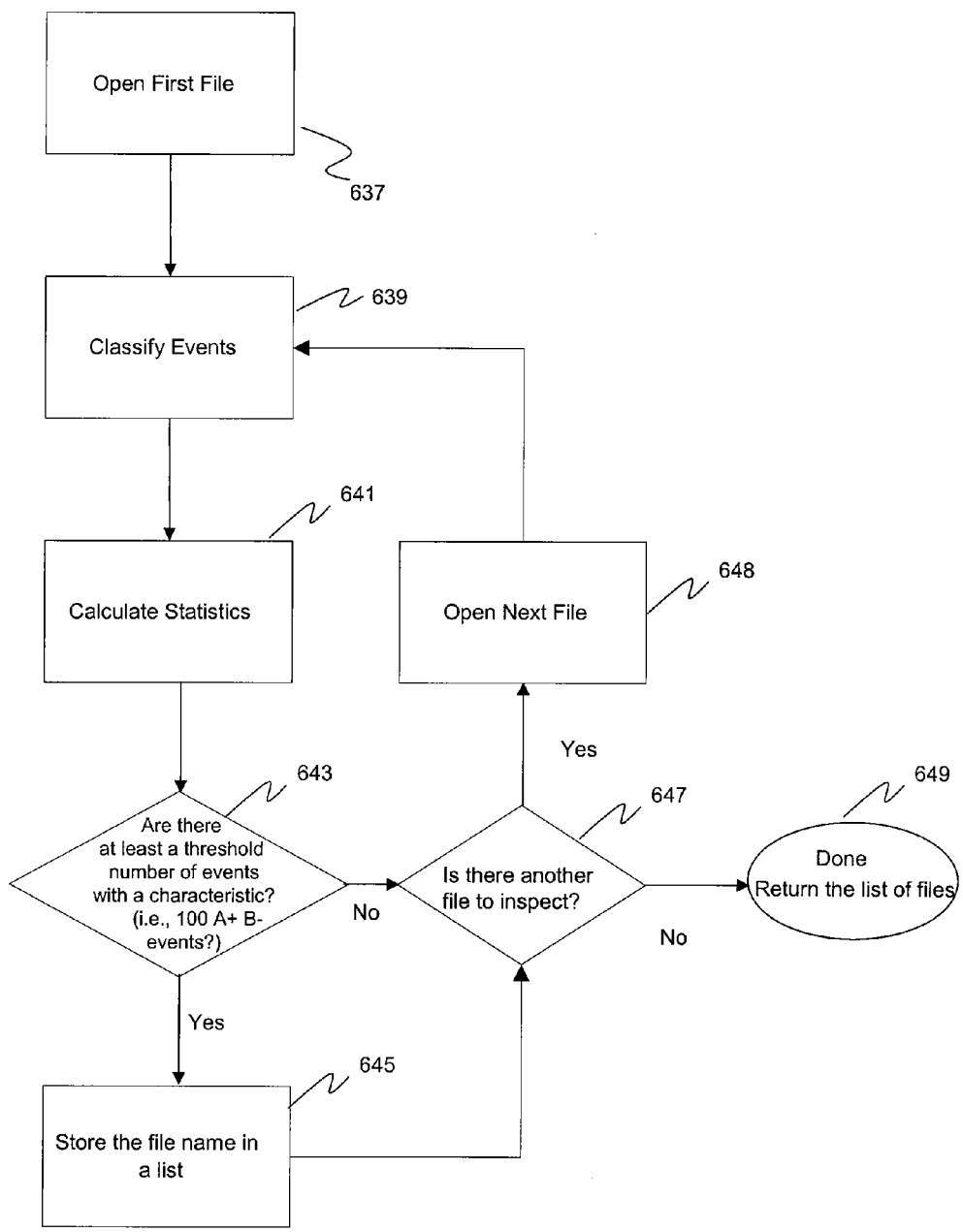
FIG. 6 illustrates data mining operations.

FIG. 6 is a flowchart illustrating a traditional data mining operation 600. For example, FIG. 6 may depict the steps involved in finding all data files having at least 100 A+ B− events. In one example, the data files can include FCS files 103 or other currently-available file formats. Data mining begins in step 637 by opening a first data file. In one example, step 637 may or may not include populating a raw measurements table, for example populating table 417 as described above with reference to step 524 in FIG. 5A. After the first data file is opened, method 600 moves to step 639. In this example of traditional data mining operation 600, the data mining tool, e.g., data mining device 113, does not store raw measurements from the first data file in an extensible star schema database, such as star schema database 105 described herein.

In step 639, events are classified. However, unlike steps 418 and 528 described above, in this example step 639 does not populate classified events table 419 in a star schema database, such as star schema database 105. After events from the first data file are classified, method 600 moves to step 641.

In step 641, statistics are calculated. After statistics are calculated, method 600 moves to step 643. However, in this example, unlike step 420 described above, statistic calculation does not populate a statistics table, e.g., table 422 in star schema database 105. After events from the first data file are classified, method 600 moves to step 643.

In step 643, a determination is made regarding whether there are at least a user-selected threshold number of events with shared characteristics. In the example depicted in FIG. 6, a determination is made regarding whether there are 100 events that are A+ B−. If it is determined in step 643 that there are at least a threshold number of events with a desired characteristic, method 600 moves to step 645. In the example depicted in FIG. 6, if there are at least 100 events that are A+ B−, the method moves to step 645. If it is determined in step 643 that there are not at least a threshold number of events that have a certain characteristic, method 600 moves to step 647. In the example scenario depicted in FIG. 6, if there are not at least 100 events that are A+ B−, method 600 moves to step 647.

In step 645, the file name is stored in a list. After storing the file name in a list, method 600 moves to step 647.

In step 647, an evaluation is made regarding whether another data file is available to inspect. If there is another data file to inspect, the next data file is opened in step 648. In step 648, after the next data file is opened, a command is given and steps 639-647 are repeated. If it is determined in step 647 that no other data files have been received, method 600 moves to step 649 where the process ends.

One drawback to this exemplary operation is that it is costly (in terms of time) to classify events and calculate statistics in steps 639 and 641. For example, when using currently available computers to implement traditional methods depicted in method 600, it can take days to search through datasets comprising a large number of data files. Data mining methods and systems according to embodiments of the present invention, and described below with reference to FIGS. 7-9, offer significant improvements over this exemplary method.

4.1 Exemplary Data Mining with the Star Schema Database and User Interface

Figure 7:
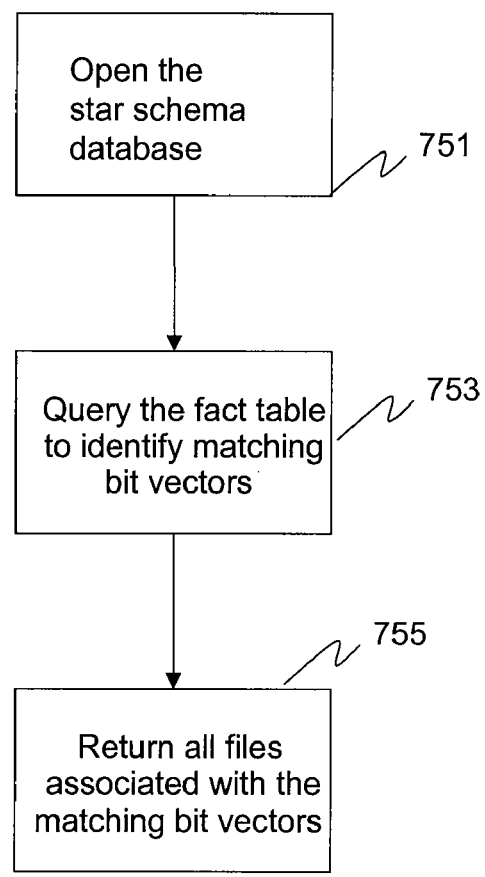
FIG. 7 is a flowchart representing a method for data mining using a star schema database, according to an embodiment of the invention.

FIG. 7 is a flowchart depicting a method 700 illustrating steps by which data mining is performed, according to an embodiment of the invention.

In the example shown, method 700 illustrates the steps by which data is mined from star schema database 105. Method 700 is described with reference to the embodiments of FIGS. 1-5. However, method 700 is not limited to those example embodiments.

The method begins at step 751, where star schema database 105 is opened. After star schema database 105 is opened, a query 220 is generated by query builder 214 corresponding to attributes 216 and constraints 218 selected by user 227 using user interface 111. In the example depicted in FIG. 7, the query involves finding all data files having at least a user-selected threshold number of events with shared characteristics. In an exemplary embodiment, the query can involve finding all data files having at least 100 A+ B− events, similar to the exemplary query depicted in FIG. 6. After star schema database 105 is opened and the query 220 is generated by query builder 214, method 700 moves to step 753.

In step 753, a fact table in star schema database 105 is queried. In one example, a fact table, such as fact table 306 or fact table 310, is queried by query executor 215 to identify matching bit vectors. In an embodiment, step 753 queries bit vectors table 531 to find matching bit vectors. After matching bit vectors are identified, method 700 moves to step 755.

In step 755, all data files associated with matching bit vectors identified in step 753 are returned. According to an embodiment of the present invention, the data files are FCS files 103. For example, data from FCS files 103 may be displayed in user display 111 for user 227. In an embodiment of the invention, database query results 224 corresponding to the returned data files are displayed 226 in user interface 111, wherein the data files may be correlated to database records in star schema database 105 by patient identifiers.

In one example, the query results 224 are available after only one or two queries against star schema database 105. For example, query builder 214 and query executor 215 are able to find and return data from data files containing at least 100 A+ and B− events after only one or two queries without having to scan data files. For example, using the populated star schema database 105 data files, such as FCS files 103, may not need to be scanned multiple times in order to display query results.

FIGS. 8 and 9 illustrate a graphical user interface (GUI), according to an embodiment of the present invention. For example, the GUI may be associated with user interface 111 of FIGS. 1 and/or 2. In an embodiment, system 100 includes an output device configured to control a display on user interface 111 to display the GUI depicted in FIGS. 8 and 9. In accordance with an embodiment shown in FIGS. 8 and 9, user interface 111 comprises a plurality of regions, e.g., first to fourth regions 820, 822, 824, and 826, and each region 820, 822, 824, and 826 has a plurality of command regions 825. For example, first region 820 is used to select query attributes, e.g., attributes 216 in FIG. 2. System 100 also includes input device 112, which is configured to allow user 227 to select among respective command regions 825, for example through moving a pointer or cursor on the GUI, within each of the plurality of regions 820, 822, 824, and 826 to choose an attribute 216, constraint 218, file, or result records 823 associated with the command regions. According to embodiments of the present invention, the input device can be, but is not limited to, for example, a pointing device, a track ball, a touch pad, a joy stick, a voice activated control system, rotary dials, a touch screen, or other input devices used to provide interaction between user 227 and user interface 111.

Selectable query attributes 216 are displayed in first region 820 of user interface 111. For example, this allows for associating one or more of the selectable query attributes 216 in first region 820 with dimensions stored in one or more dimension tables 304 (FIG. 3) based on using the input device to move the selectable query attributes 216 from first region 820 to second region 822. Second region 822 can be conceptualized as a report or results area of user interface 111. In an embodiment, the movement of query attributes 216 is done with a drag-and-drop operation between first region 820 and second region 822. Query builder 214 generates an appropriate query 220 based upon the attributes 216 selected in first region 820, query executor 215 then runs the query 220, and the corresponding query results 224 such as result records 823 are displayed 226 in second region 822.

According to an embodiment of the present invention, system 100 includes a data filter that uses user-selectable query constraints 218 in third region 824 of user interface 111. The data filter controls the processing and display of a subpopulation of query results 224 in second region 822 based on user-selected query constraints 218 in third region 824. In embodiments of the present invention, query constraints 218 may be based upon one or more of string search parameters, logic operations, numerical constraints, Boolean operations, etc. inputted by user 227 in third region 824. In the example embodiment depicted in FIG. 8, user 227 has selected a constraint 218 corresponding to the CytometerSerialNumber field in the Equipment dimension table 304 depicted in FIG. 3. In the example shown in FIG. 8, user 227 has selected cytometer serial number constraint 218 with values equaling Z14103 so that only data records captured by flow cytometer serial number Z14103 are displayed in second region 822. This filtering by cytometer serial number is performed on an ad-hoc basis by the data filter. In this way, user interface 111 allows user 227 to perform "what if" analyses by iteratively selecting attributes in first region 820 and applying constraints from third region 824.

If user 227 drags an attribute 216 from first region 820 (i.e., the attribute region) to third region 824 (i.e., the constraints region), user 227 is able to filter (or constrain) the result rows that are displayed in the report area of second region 822.

According to an embodiment, system 100 includes an output device which is controlled to display the graphical depiction of raw event data 102 in fourth region 826 based on using the input device to select results in second region 822. In another embodiment, system 100 includes an output device that is controlled to display the graphical depiction of data from FCS files 103 in fourth region 826 based on using the input device to select results in second region 822. For example, the output device may be configured to be controlled to display scatter plots, polychromatic dot plots, graphs, histograms, hierarchical tree plots, star coordinate plots, etc. corresponding to flow cytometry data in fourth region 826.

In an embodiment, data in data warehouse 105 includes patient identifiers that can be used by the output device to display a subpopulation of query results in second region 822, which are correlated with flow cytometer data displayed in fourth region 826. For example, the output device can control graphically depicting of raw event data 102 and data from FCS files 103 in fourth region 826 that correspond to a user-selected subset or subpopulation of the query results displayed in second region 822. In an embodiment, user 227 may select a query result record 823 in second region 822 by clicking on the result record 823 and the corresponding raw event data 102 or data from FCS files 103 graphically depicted in fourth region 826. For example, when a row in second region 822 is selected by user 227, dot plots and histograms are extracted from raw event data 102 or FCS files 103, and one of them is displayed in fourth region 826. User 227 can click on the X axis or Y axis label in fourth region 826 to change a parameter (such as FS or SS depicted in FIG. 9) that is graphically displayed in fourth region 826. In this way, data mining device 113 can be used to find subsets of FCS files 103 or raw event data 102 that satisfy or meet some criteria of a clinician or investigator. After the FCS files 103 have been identified, the investigator can further analyze related data within star schema database 105 that corresponds to the details of graphically depicted data displayed in fourth region 826.

FIG. 9 depicts the "study" feature of data mining device 113. In the example embodiment illustrated in FIG. 9, user 227 has selected the ProtocolName attribute in second region 822, pressed a right click with the input device, and then selected the GROUP feature. This results in having a subpopulation 930 of results records 823 grouped by the ProtocolName. User 227 can use the input device to select STUDY link 932 that is located to the right of ProtocolName (the protocol name is "AB642/MBA-MD-648 MAGGIE" in the specific example depicted in FIG. 9). In an embodiment, selection of STUDY link 932 causes dialog box 934 to be displayed by the output device on user interface 111. Dialog box 934 displays the range of raw event data 102 or FCS file 103 data corresponding to subpopulation 930 of results records 823. User 227 can now move horizontal slider 935 to review all of the data within raw event data 102 or FCS files 103 that make up the selected study. The study data is graphically depicted in a plurality of dot plots, polychromatic scatter plots, histograms, or hierarchical tree plots, similar to the graphical display in fourth region 826 described above.

5. Example Computer Implementation

Figure 10:
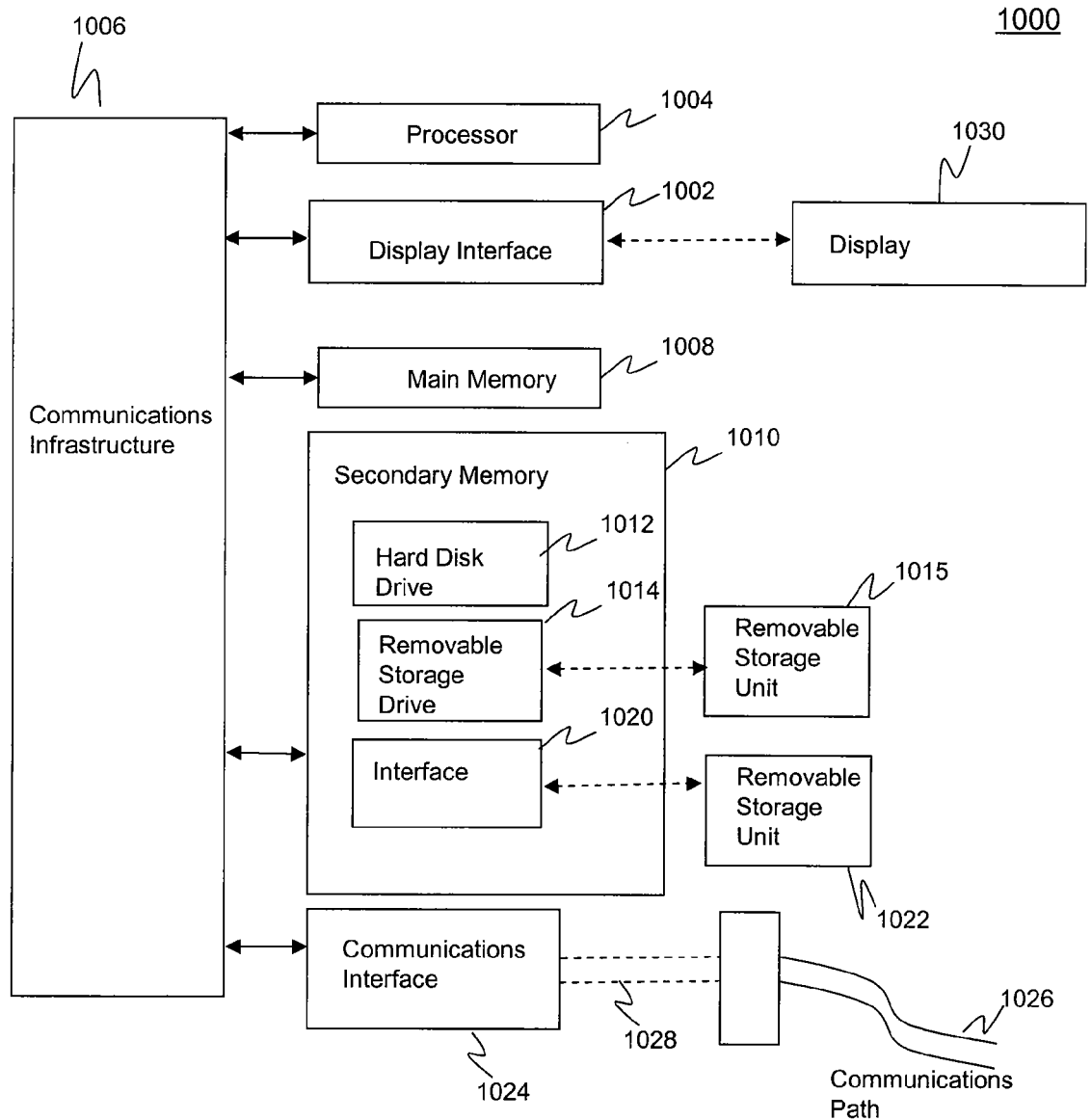
FIG. 10 illustrates an example computer system useful for implementing components, according to an embodiment of the invention.

Various aspects of the present invention can be implemented by software, firmware, hardware, or a combination thereof. FIG. 10 illustrates an example computer system 1000 in which the present invention, or portions thereof, can be implemented as computer-readable code. For example, the methods illustrated by flowcharts 400, 500, and 700 of FIGS. 4, 5, and 7 can be implemented in system 1000. Various embodiments of the invention are described in terms of this example computer system 1000. After reading this description, it will become apparent to a person skilled in the relevant art how to implement the invention using other computer systems and/or computer architectures.

Computer system 1000 includes a display interface 1002. The display interface may be integrated with user interface 111 and data mining interface 113 depicted in FIG. 1. Connected to the display interface may be display 1030. Display 1030 may be used for user interface 111 and a data mining device 113. The display may be integral with the flow cytometer system 100 or it may be a separate component. Computer system 1000 includes one or more processors, such as processor 1004. Processor 1004 can be a special purpose or a general purpose processor. Processor 1004 is connected to a communication infrastructure 1006 (for example, a bus, or network).

Computer system 1000 also includes a main memory 1008, preferably random access memory (RAM), and may also include a secondary memory 1010. Secondary memory 1010 may include, for example, a hard disk drive 1012, a removable storage drive 1014, flash memory, a memory stick, and/or any similar non-volatile storage mechanism. Removable storage drive 1014 may comprise a floppy disk drive, a magnetic tape drive, an optical disk drive, a flash memory, or the like. The removable storage drive 1014 reads from and/or writes to a removable storage unit 1015 in a well known manner. Removable storage unit 1015 may comprise a floppy disk, magnetic tape, optical disk, etc. which is read by and written to by removable storage drive 1014. As will be appreciated by persons skilled in the relevant art(s), removable storage unit 1015 includes a computer usable storage medium having stored therein computer software and/or data.

In alternative implementations, secondary memory 1010 may include other similar means for allowing computer programs or other instructions to be loaded into computer system 1000. Such means may include, for example, a removable storage unit 1022 and an interface 1020. Examples of such means may include a program cartridge and cartridge interface (such as that found in video game devices), a removable memory chip (such as an EPROM, or PROM) and associated socket, and other removable storage units 1022 and interfaces 1020 which allow software and data to be transferred from the removable storage unit 1022 to computer system 1000.

Computer system 1000 may also include a communications interface 1024. Communications interface 1024 allows software and data to be transferred between computer system 1000 and external devices. Communications interface 1024 may include a modem, a network interface (such as an Ethernet card), a communications port, a PCMCIA slot and card, or the like. Software and data transferred via communications interface 1024 are in the form of signals which may be electronic, electromagnetic, optical, or other signals capable of being received by communications interface 1024. These signals are provided to communications interface 1024 via a communications path 1026. Communications path 1026 carries signals and may be implemented using wire or cable, fiber optics, a phone line, a cellular phone link, an RF link or other communications channels 1028.

In this document, the terms "computer program medium" and "computer usable medium" are used to generally refer to media such as removable storage unit 1018, removable storage unit 1022, and a hard disk installed in hard disk drive 1012. Signals carried over communications path 1026 can also embody the logic described herein. Computer program medium and computer usable medium can also refer to memories, such as main memory 1008 and secondary memory 1010, which can be memory semiconductors (e.g. DRAMs, etc.). These computer program products are means for providing software to computer system 1000.

Computer programs (also called computer control logic) are stored in main memory 1008 and/or secondary memory 1010. Computer programs may also be received via communications interface 1024. Such computer programs, when executed, enable computer system 1000 to implement the present invention as discussed herein. In particular, the computer programs, when executed, enable processor 1004 to implement the processes of the present invention, such as the steps in the methods illustrated by flowcharts 400 and 500 of FIGS. 4 and 5 discussed above. Accordingly, such computer programs represent controllers of the computer system 1000.

Where the invention is implemented using software, the software may be stored in a computer program product and loaded into computer system 1000 using removable storage drive 1014, interface 1020, hard drive 1012, or communications interface 1024.

The invention is also directed to computer program products comprising software stored on any computer useable medium. Such software, when executed in one or more data processing device, causes a data processing device(s) to operate as described herein. Embodiments of the invention employ any computer useable or readable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage device, etc.), and communication mediums (e.g., wired and wireless communications networks, local area networks, wide area networks, intranets, etc.).

6. Conclusion

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method comprising:
   (a) creating a first extensible dimension table, wherein the columns of the first extensible dimension table include keywords from received data,
   (b) creating a second extensible dimension table, wherein the columns of the second extensible dimension table correspond to parameters from the received data;
   (c) receiving classified data, wherein the classified data is classified based on characteristics of subpopulations of received data;
   (d) populating the first and second extensible dimension tables with data describing values of dimensions of the classified data;
   (e) populating a first fact table with the classified data;
   (f) populating a second fact table with a summary of the data from the first fact table; and
   (g) storing the populated tables in a computer useable storage medium,
   wherein the first fact table and the second fact table both point to the second extensible dimension table.

2. The method of claim 1, further comprising:
   monitoring for subsequent received data, wherein the subsequent received data is received after step (d); and if the monitoring step discovers subsequently received data:
(h) modifying the first extensible dimension table to include columns corresponding to keywords from the subsequently received data;
(i) modifying the second extensible dimension table to include columns corresponding to parameters from the subsequently received data; and
repeating steps (c)-(g).

3. The method of claim 1, wherein the received data is data received from a flow cytometer instrument.

4. The method of claim 1, further comprising: parsing the received data before step (a) to determine if the data contains phenotypic classifiers.

5. The method of claim 4, wherein step (e) father comprises populating the first fact table with classified data including phenotypic classifiers.

6. The method of claim 1, further comprising:
(h) modifying a third extensible dimension table to include columns having region identifiers associated with the first fact table, wherein the region identifiers identify regions within the event data.

7. The method of claim 3, further comprising including at least a sample identifier in the received data.

8. The method of claim 7, further comprising:
determining proteomic data in the received data; and
correlating the flow cytometry data with the proteomic data based upon the sample identifier.

9. The method of claim 7, further comprising:
determining genomic data in the received data; and
correlating the flow cytometry data with the genomic data based upon the sample identifier.

10. The method of claim 9 wherein the sample identifier is a patient identifier.

11. A non-transitory computer-readable storage medium having computer program code recorded thereon that, when executed by a processor, causes the processor to perform a method, the method comprising:
creating a first extensible dimension table, wherein the columns of the first extensible dimension table include keywords front received data;
creating a second extensible dimension table, wherein the columns of the second extensible dimension table correspond to parameters from the received data;
receiving classified data, wherein the classified data is classified based on characteristics of subpopulations of received data;
populating the first and second extensible dimension tables with data describing values of dimensions of the classified data;
populating a first fact table with the classified data; and
populating a second fact table with a summary of the data from the first fact table,
wherein the first fact table and the second fact table both point to the second extensible dimension table.

12. A computer system comprising:
a processor executing a program comprising:
a first dimension creating module configured to create a first extensible dimension table, wherein the columns of the first extensible dimension table include keywords from received flow cytometry data;
a second dimension creating module configured to create a second extensible dimension table, wherein the columns of the second extensible dimension table correspond to parameters from the received data;
a data receiving module configured to receive classified data, wherein the classified data is classified based on characteristics of subpopulations of received data;
a dimension populating module configured to populate the first and second extensible dimension tables with data describing values of dimensions of the classified data;
a first fact populating module configured to populate a first fact table with the classified data; and
a second fact populating module configured to populate a second fact table with a summary of the data from the first fact table,
wherein the first fact table and the second fact table both point to the second extensible dimension table.

13. A method for storing data in a data warehouse comprising the steps of:
creating a star schema with a computer by:
(a) creating a first dimension table;
(b) creating a second dimension table;
(c) creating a first fact table;
(d) creating a second fact table;
populating the first fact table with a summary of the classified data;
populating the second fact table with a summary of data from the first fact table; and
storing the populated tables in a computer useable storage medium
wherein the first fact table and the second fact table both point to the second dimension table,
wherein the first dimension table comprises attributes of the classified data, and
wherein the second dimension table comprises parameters of the classified data.

14. The method of claim 13, further comprising:
(e) monitoring received data, wherein the received data is receive (after the first fact table is populated; and
(f) modifying the first dimension table to include columns corresponding to keywords from the received data; and
(g) modifying the second dimension table to include columns corresponding to parameters from the received data.

* * * * *